US012779085B2

(12) United States Patent
Ashrafi et al.

(10) Patent No.: US 12,779,085 B2
(45) Date of Patent: Nov. 3, 2026

(54) RADIOPAQUE POLYMERS

(71) Applicant: BIOCOMPATIBLES UK LIMITED, Farnham (GB)

(72) Inventors: Koorosh Ashrafi, Purley (GB); Hugh Britton, Gillingham (GB); Francesco Cuda, Basingstoke (GB); Andrew Lennard Lewis, Farnham (GB); Cristian Parisi, Boston, MA (US); Yiqing Tang, Guildford (GB); Sean Leo Willis, Farnham (GB)

(73) Assignee: BIOCOMPATIBLES UK LIMITED, Farnham (GB)

( * ) Notice: Subject to any disclaimer, the term of this patent is extended or adjusted under 35 U.S.C. 154(b) by 283 days.

(21) Appl. No.: 18/354,109

(22) Filed: Jul. 18, 2023

(65) Prior Publication Data

US 2023/0355833 A1 Nov. 9, 2023

Related U.S. Application Data

(62) Division of application No. 16/933,042, filed on Jul. 20, 2020, now Pat. No. 11,744,916.

(30) Foreign Application Priority Data

Jul. 18, 2019 (GB) ...................................... 1910286

(51) Int. Cl.

*A61L 24/06* (2006.01)
*C07D 405/04* (2006.01)
*C08F 216/10* (2006.01)

(52) U.S. Cl.

CPC ............ *A61L 24/06* (2013.01); *C07D 405/04* (2013.01); *C08F 216/10* (2013.01); *A61L 2430/36* (2013.01)

(58) Field of Classification Search

CPC ................ A61K 49/04; A61K 49/0433; A61K 49/0438; A61K 49/0442; A61K 49/0476

See application file for complete search history.

(56) References Cited

U.S. PATENT DOCUMENTS

| | | | |
|---|---|---|---|
| 4,323,699 | A | 4/1982 | Norval |
| 4,406,878 | A | 9/1983 | DeBoer |
| 6,235,836 | B1 | 5/2001 | Kim et al. |
| 2001/0020065 | A1 | 9/2001 | Kim et al. |
| 2013/0108574 | A1 | 5/2013 | Chevalier et al. |
| 2016/0228556 | A1 | 8/2016 | Hohn et al. |

FOREIGN PATENT DOCUMENTS

| | | | |
|---|---|---|---|
| CN | 105968244 | A | 9/2016 |
| EP | 1156034 | A2 | 11/2001 |
| EP | 2365009 | A1 | 9/2011 |
| JP | H09188716 | A | 7/1997 |
| JP | 5008934 | B2 | 8/2012 |
| JP | 2013521087 | A | 6/2013 |
| WO | 2004071495 | A1 | 8/2004 |
| WO | 2011110589 | A1 | 9/2011 |
| WO | 2014152488 | A2 | 9/2014 |
| WO | 2015003309 | A1 | 1/2015 |
| WO | 2015033092 | A1 | 3/2015 |

OTHER PUBLICATIONS

Ashrafi et al., “Characterization of a Novel Intrinsically Radiopaque Drug-Eluting Bead for Image-Guided Therapy: DC Bead Lumi (TM)”, Journal of Controlled Release, ElSevier Amsterdam, NL vol. 250, pp. 36-47, Feb. 8, 2017.

Mawad et al., “Elaboration of Radiopaque Iodinated Nanoparticles for in Situ Control of Local Drug Delivery” Biomaterials, vol. 30, pp. 5667-5674, 2009.

Shpuntov et al., “Effective Synthesis of 3-(2-furyl)phthalides Under the Friedel-Crafts Reaction Conditions”, Chemistry of Heterocyclic Compounds, vol. 50, No. 12, Mar. 2015 (Year 2015).

International Search Report and Written Opinion for the International Patent Application No. PCT/IB2020/056803, dated Sep. 24, 2020, 11 pages.

*Primary Examiner* — James W Rogers

(74) *Attorney, Agent, or Firm* — Seager, Tufte & Wickhem, LLP

(57) ABSTRACT

The present disclosure relates to radiopaque PVA polymers where the PVA has a first pendant group and a second pendant group, wherein the first pendant group comprises a first phenyl group bearing 1 to 5 iodine atoms, and the second pendant group comprises either (a) a second phenyl group bearing 1 to 3 substituents selected from the group W and optionally 1 to 4 iodine substituents, the group(s) W and the optional iodines being the sole substituents of the second phenyl group. Each W is selected from —OH, —COOH, $—SO_3H$, $—OPO_3H_2$, —O—($C_{1-4}$alkyl), —O—($C_{1-4}$alkyl)OH, —O—($C_{1-4}$alkyl)$R^2$, —O—$(C_2H_5O)_q$$R^1$—(C═O)—O—$C_{1-4}$alkyl and —O—(C═O)$C_{1-4}$alkyl; wherein $R^1$ is H or $C_{1-4}$ alkyl; $R^2$ is —COOH, $—SO_3H$, or $—OPO_3H_2$; q is an integer from 1 to 4; wherein the group W may be in the form of a pharmaceutically acceptable salt; or (b) a pyridyl group; which is optionally in the form of a pyridinium ion.

20 Claims, 1 Drawing Sheet

RADIOPAQUE POLYMERS

CROSS-REFERENCE TO RELATED APPLICATIONS

This application is a divisional of U.S. patent application Ser. No. 16/933,042, filed Jul. 20, 2020, which claims the benefit of priority to Application No. GB 1910286.2, filed Jul. 18, 2019 and entitled "RADIOPAQUE POLYMERS", the disclosure of which is hereby incorporated by reference in its entirety.

BACKGROUND

This present disclosure relates to radiopaque polymers and to their use, particularly in the manufacture of medical devices and in methods of medical treatment. The present disclosure particularly relates to radiopaque polymers useful in the field of therapeutic embolisation.

Therapeutic embolisation is a minimally invasive procedure in which a material is introduced into a blood vessel to produce an occlusion in order to slow or stop blood flow or to fill a space such as an aneurism. This approach has been useful in the treatment of conditions such as, gastrointestinal bleeding, arteriovenous malformations, hypervascular tumours such as hepatocellular carcinoma, benign growths such as uterine fibroids and more recently benign prostate hyperplasia (BPH).

Biocompatible microspheres are useful embolic agents because they can be easily delivered to the target site and can be provided in defined size ranges for more predictable embolisation according to the vessel size. Liquid embolics have also found utility in some areas, using materials that are delivered as a liquid, but which gel, solidify or precipitate in situ. Some such systems rely on polymerisation or gel formation in situ, whilst others rely on delivery of a material in a carrier, such as an organic solvent, which rapidly dissipates in the blood leaving behind the embolic material. Liquid embolics have the added advantage that they conform to the vessel wall and, depending on their deposition characteristics, typically form a unified embolus, rather than discrete spheres. Typically such embolic materials are synthetic or natural polymers, which are chosen to provide desired properties such as biocompatibility, density, compressibility, flowability and ease of catheter delivery. Some may also be designed to load drugs for delivery at the site of deposition. For liquid embolics, properties such as flow characteristics in the vessel and in the delivery catheter, speed and predictability of deposition and robustness of the embolus are also important.

Radiopaque polymers having iodinated groups covalently coupled to the polymer backbone have been proposed (e.g. WO2015/033092). Radiopaque liquid embolics having iodinated groups coupled to the polymer backbone have also been described (e.g. WO2011/110589). The presence of sufficient iodinated groups on these polymers renders the materials visible using X-ray based techniques, but also leads to changes in the handling and other characteristics compared to the native polymer. Iodination may lead to unpredictable or rapid precipitation on leaving the catheter, undesirable behaviour in the blood vessel such as "stringing" of the polymer, and other unfavourable handling characteristics. It is desirable therefore to provide improved iodinated polymers that are sufficiently radiopaque to be visible on X-ray, but have improved usability properties.

BRIEF SUMMARY

The present inventors have identified that one or more of the above issues can be addressed by the polymers described herein. Thus in a first aspect, the present disclosure provides a polymer comprising polyvinyl alcohol (PVA), the PVA having a first pendant group and a second pendant group, wherein the first pendant group comprises a first phenyl group bearing 1 to 5 iodine atoms as the sole substituent(s) of the first phenyl group (i.e., the sole non-hydrogen substituent(s) on the first phenyl group), and wherein the second pendant group comprises a group selected from: (a) a second phenyl group bearing 1 to 3 substituents selected from the group W and optionally 1 to 4 iodine substituents, the group(s) W and the optional iodines being the sole substituents of the second phenyl group (i.e., the sole non-hydrogen substituent(s) on the second phenyl group); wherein each W is independently selected from —OH, —COOH, —$SO_3H$, —$OPO_3H_2$, —O—($C_{1-4}$alkyl), —O—($C_{1-4}$alkyl)OH, —O—($C_{1-4}$alkyl)$R^2$, —O—$(C_2H_5O)_q R^1$, —(C═O)—O—$C_{1-4}$alkyl and —O—(C═O)$C_{1-4}$alkyl; wherein $R^1$ is H or $C_{1-4}$ alkyl; $R^2$ is —COOH, —$SO_3H$, or —$OPO_3H_2$; wherein q is an integer from 1 to 4; and wherein the group W may be in the form of a pharmaceutically acceptable salt; and (b) a pyridyl group; which is optionally in the form of a pyridinium ion.

The pyridinium group may, for example be in the form of a pharmaceutically acceptable salt with an anion, such as a halide (e.g. chloride or iodide but preferably chloride).

Thus, in the polymer, a PVA backbone comprises two types of pendant groups. The sum of the number of iodines and the number of W groups on the second pendant group will not exceed 5, and in some embodiments does not exceed 4. Each pendant group is typically coupled via one or more hydroxyl groups of the PVA polymer back bone. Each pendant group is typically coupled via a single coupling group to the PVA.

The inventors have identified that PVA polymers may be rendered radiopaque by providing to the polymer, a first pendant group comprising a phenyl group to which is coupled, one or more iodines. Increasing either the number of iodines coupled to the phenyl group or the number of pendant groups coupled to the backbone, increases the radiopacity of the polymer, however at the same time it also increases the hydrophobic nature of the polymer due inter alia to (i) the quantity of iodine added and (ii) a decrease in the number of free hydroxyls with each pendant group coupled. This makes tuning the properties of the polymer challenging.

The present inventors have now also determined that hydrophobicity and radiopacity may be effectively balanced by providing a combination of a first pendant group having only iodines attached to the phenyl group and to modulate the hydrophobicity of the polymer by providing a second pendant group carrying only one or more hydrophilic substituent(s) (W). The balance between the hydrophobic and hydrophilic natures of the polymer can then be tuned by increasing or decreasing the proportion of the second pendant group coupled, in relation to the first, in order to modulate the properties. Alternatively, hydrophilicity/radiopacity can be tuned by providing a second pendant group which carries one or more iodines in addition to the hydrophilic group (W).

Thus in one embodiment, the second pendant group comprises only one, two or three, typically one or two and more typically one W group as the sole substituents of the phenyl group. In a further embodiment, the second pendant group carries one, two or three, typically one or two and more typically one W group and additionally carries one or more iodines, preferably 1, 2 or 3 iodines as the sole substituent(s) of the phenyl group.

For the second pendant group, the following combinations are beneficial: 1 or 2 W groups and no iodines, one W group and 1 iodine, one W group and 2 iodines, one W group and 3 iodines.

Beneficial W groups are —OH, —COOH, —$SO_3H$, —O—($C_{1-4}$alkyl), —O—($C_{1-4}$alkyl)OH, —O—($C_{1-4}$alkyl)$R^2$, —O—$(C_2H_5O)_q R^1$—(C═O)—O—$C_{1-4}$alkyl and —O—(C═O)$C_{1-4}$alkyl; wherein:

$R^1$ is H or $C_{1-4}$ alkyl, typically H or methyl, particularly methyl;

$R^2$ is —COOH, or —$SO_3H$ and typically —$SO_3H$; and q is an integer from 1 to 4.

More typical W groups are —OH, —COOH, —$SO_3H$, —O—($C_{1-4}$alkyl)$R^2$ and —O—$(C_2H_5O)_q R^1$; particularly —$SO_3H$ and —O—($C_{1-4}$alkyl)$R^2$; wherein $R^1$ is H or $C_{1-4}$ alkyl, typically H or methyl, particularly methyl; $R^2$ is —COOH, or —$SO_3H$ and typically —$SO_3H$; and q is an integer from 1 to 4.

In any of the polymers herein, where W is —O—($C_{1-4}$alkyl)$R^2$, it may be —O—($C_{2-4}$alkyl)$R^2$ and more typically —O—($C_3$alkyl)$R^2$ or —O—($C_4$alkyl)$R^2$.

The first pendant group may be coupled to the PVA backbone in any manner available in the art, but is typically coupled through the alcoholic hydroxyl groups of the PVA backbone. Coupling through these groups makes available several coupling chemistries, in order to provide coupling groups such as ether, ester, amide or 1,3 dioxane. By 1,3 dioxane is meant a coupling group as below, in which the pendant group is coupled through two adjacent hydroxyls of the PVA back bone to form a dioxane ring. This is also described elsewhere as a cyclic acetal linkage (e.g. WO2015/033092), e.g.:

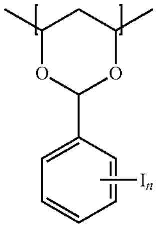

The second pendant group may also be coupled to the PVA backbone in any manner available in the art, but is also typically coupled through the alcoholic hydroxyl groups of the PVA backbone, particularly through linkages such as ether, ester, amide and 1,3 dioxane.

In each case, independently, the linkage may beneficially be an ether, amide or 1,3 dioxane, more typically, independently, an ether or 1,3 dioxane group and particularly by a 1,3 dioxane in each case. Esters are less preferred since such linkages may hydrolyse slowly in the body, releasing the pendant group. Beneficially, either the first pendant group is coupled to the PVA through an ether linkage and the second pendant group is coupled to the PVA through a 1,3 dioxane group or both the first pendant group and the second pendant group are coupled to the PVA through a 1,3 dioxane group. In particular embodiments, both are coupled through a 1,3 dioxane group.

The first pendant group is beneficially a group according to formula 1A or 1B:

1A

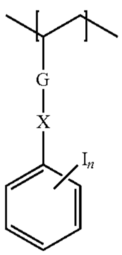

1B

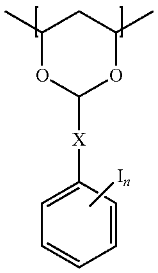

wherein

X is independently either a bond (such that the phenyl is directly bonded to the coupling group) or is a linking group. Typically the linking group has a chain of 1 to 6 atoms selected from C, N, S and O, directly between the phenyl group and the coupling group, provided that the chain contains no more than one atom selected from N, S and O; wherein C is optionally substituted by a group selected $C_{1-4}$ alkyl; wherein N is substituted by $R^3$, wherein $R^3$ is selected from H and $C_{1-4}$ alkyl; and wherein S is either an —S(O)— or —$S(O)_2$— group.

By "directly between", is meant that that a direct link can be traced between the phenyl and the coupling group, comprising only these atoms. Of these linkers, X, those in which the chain comprises S are less beneficial. Alkyl substituents of C may be —$CH_3$ or —$(CH_3)_2$ groups; $R^3$ is typically H or methyl.

Suitable linkers include, where possible, $C_{1-6}$ alkylene groups, particularly methylene or ethylene; $C_{1-5}$alkoxylene groups, groups of the formula —$(CH_2)_y$—O—$(CH_2)_z$— wherein y and z are, independently, 1, 2 or 3, and y+z is an integer from 2 to 5; and —$N(R^3)(CH_2)_{n3}$— wherein $R^3$ is H or $C_{1-4}$ alkyl, particularly H or methyl; and n3 is an integer from 1 to 4; Preferable linkers are selected from a bond, methylene and ethylene, oxymethylene and oxyethylene (where the oxygen is bonded to the phenyl), —$CH_2$—O—$CH_2$— and —NH($CH_2$)—; X is particularly a bond.

G is a coupling group through which the group of the formula 1A is coupled to the PVA and is selected from ether, ester and amide; typically ether or amide and more typically ether; and n is an integer from 1 to 5, typically 1 to 4 and more typically is 2 or 3.

Particularly beneficial first pendant groups are those of the formula:

3A

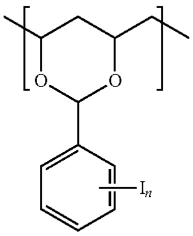

wherein n is an integer from 1 to 5; typically 1 to 4 and more typically is 2 or 3.

Beneficially the second pendant group is of the formula 2A, 2B, 2C or 2D:

2A

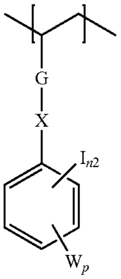

2B

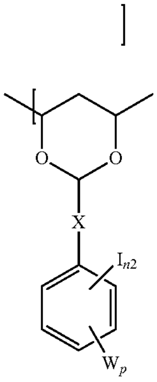

2C

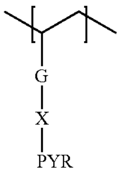

2D

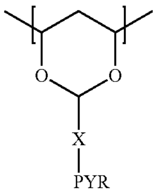

wherein PYR is a pyridyl group, for example, a 4-pyridyl group, which may be in the form of a pyridinium ion, wherein W, X and G are as defined herein n2 is independently in each case, from 0 to 4;

p is independently in each case, an integer from 1 to 3, typically 1 or 2 and more typically 1; and n2+p is independently in each case, an integer from 1 to 5.

Beneficial substitution patterns of the phenyl group of Formula 2A or 2B are:

A

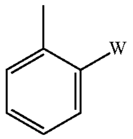

B

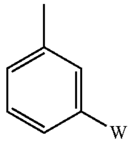

C

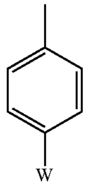

D

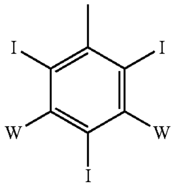

E

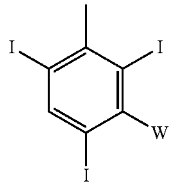

F

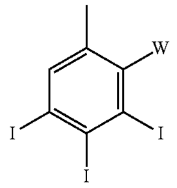

G

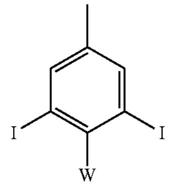

-continued

H

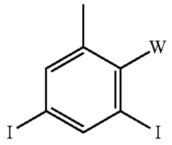

Particular rings include

I

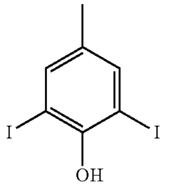

J

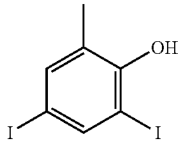

K

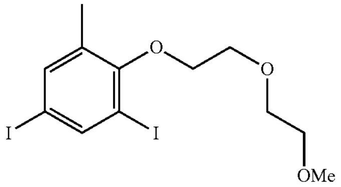

L

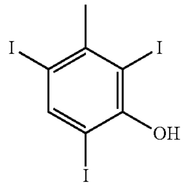

M

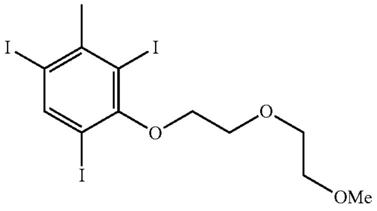

N

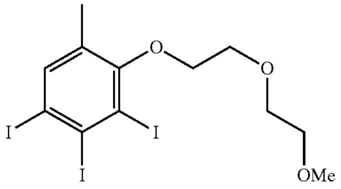

O

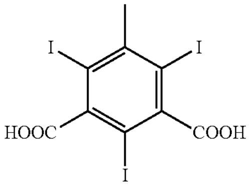

-continued

P

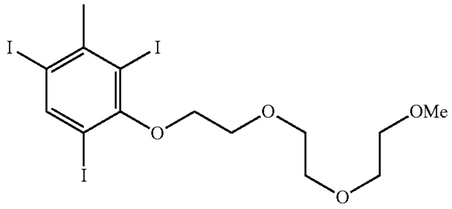

Q

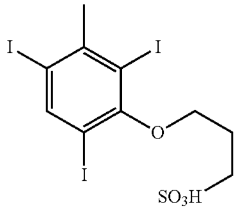

R

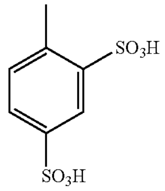

S

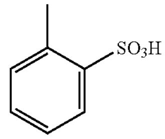

T

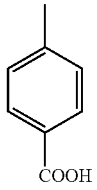

U

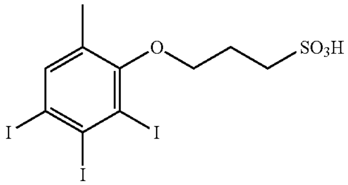

where, as elsewhere herein, acidic groups may also be in the form of any pharmaceutically acceptable salt, particularly with a group 1 metal ion such as sodium or potassium;

Particularly beneficial combinations are those:

(a) wherein the first pendant group is of the formula 4A and the second pendant group is of the formula 4B:

4A

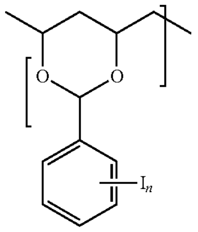

4B

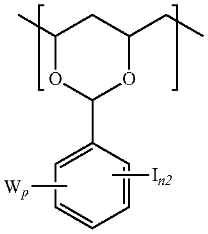

wherein n is 1, 2, 3 or 4; n2 is 1, 2, 3 or 4; W is as described above and particularly is selected from $—SO_3H$, $—O—(C_{1-4}alkyl)SO_3H$ and —COOH, more particularly $—O—(C_{1-4}alkyl)SO_3H$; and p is 1 or 2 particularly 1;

(b) wherein the first pendant group is of the formula 4A and the second pendant group is of the formula 4C:

4A

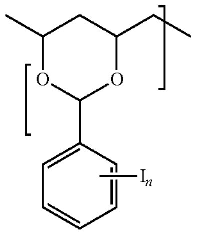

-continued

4C

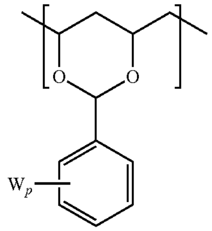

wherein n is 1, 2 or 3; W is as described above and particularly is selected from $—SO_3H$ and —COOH, more particularly $—SO_3H$; and p is 1 or 2 particularly 1; and (c) wherein the first pendant group is of the formula 4A and the second pendant group is of the formula 4D.

4A

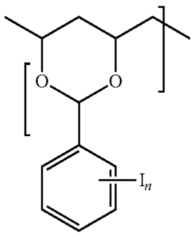

4D

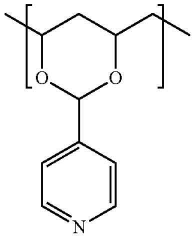

Further particularly beneficial combinations include those of Table 1 and salts thereof as described herein:

TABLE 1

| | | second pendant group | | |
|---|---|---|---|---|
| | first pendant group | Beneficial | More beneficial | |
| 1 | 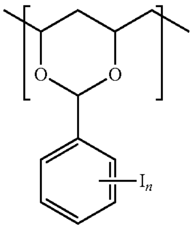 where n = 2 or 3 Particularly 2,3,5 tri iodo | 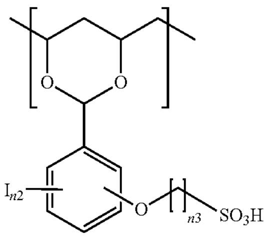 where n2 is 1,2 or 3; and n3 is 1, 2, 3 or 4 | 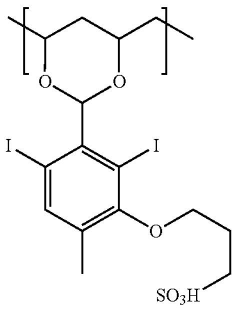 | 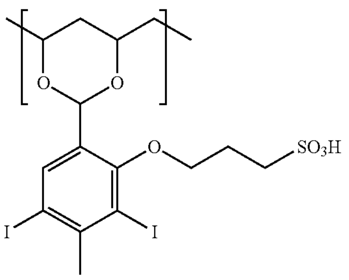 |

TABLE 1-continued

| | first pendant group | second pendant group: Beneficial | second pendant group: More beneficial |
|---|---|---|---|
| 2 | 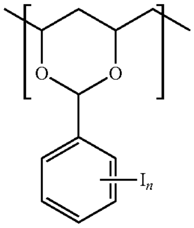 where n = 2 or 3 Particularly 2,3,5 | 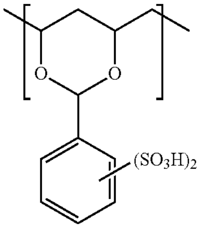 | 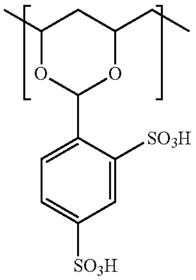 |
| 3 | 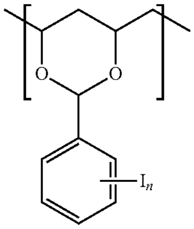 where n = 2 or 3 Particularly 2,3,5 | 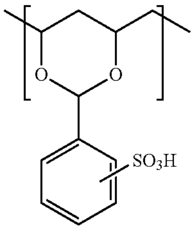 | 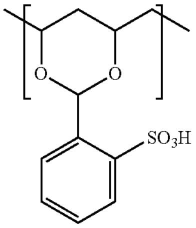 |
| 4 | 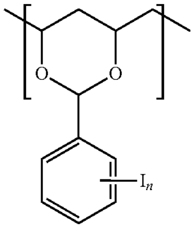 where n = 2 or 3 Particularly 2,3,5 | 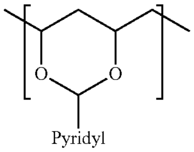 where pyridyl is 2-pyridyl, 3-pyridyl or 4-pyridyl | 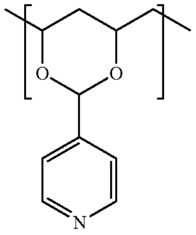 |

The first pendant group is typically present at between 0.3 to 0.7 equivalents, based on 1,3 diol groups of the native PVA (i.e., the PVA without the first and second pendant groups) polymer backbone, typically 0.4 to 0.6 equivalents. The second pendant group is typically present at a lower level. Typically the second pendant group is present at 0.01 to 0.2 equivalents, more typically 0.01 to 0.1 equivalents, based on 1,3 diol groups of the native PVA polymer backbone.

Radiopacity (or radiodensity), of the polymer may be varied by adjusting the amount of iodine in the polymer. This may be achieved by varying the number of iodines on either ring or by varying the proportion of iodine bearing pendant groups in the polymer.

Polymers of the present disclosure beneficially comprise at least 10%, typically at least 20%, more typically at least 30% and most typically at least 40% wt/wt iodine by dry weight. Polymers having at least 50% iodine by dry weight may be particularly useful in some embodiments.

Where the polymer is used to provide a liquid embolic, for example, it may be advantageous to use polymers having at least 35%, typically at least 50% and even more typically at least 55% iodine by dry weight polymer.

Iodine content may also be referred to on a volumetric basis. Iodine content is typically at least 10 mg of iodine per $cm^3$, more typically 25 mg/$cm^3$ of iodine, even more typically at least 50 mg/$cm^3$ of iodine and especially at least 100 mg/$cm^3$ of iodine. Polymers having at least 150 or 200 mg/$cm^3$ may be particularly useful in some embodiments.

Where the polymer is used to provide a liquid embolic, for example, it may be advantageous to use polymers having at least 100, typically at least 150 and even more typically at least 200 mg/ml iodine.

Volumetric iodine figures for polymers that are water swellable but not water soluble should be determined on the volume of fully hydrated polymer, for example, following precipitation of the polymer in phosphate buffered saline.

Typically the polymer has a radiodensity (calculated on the basis of precipitated/gelled polymer and excluding voids) of at least 500 HU (Hounsfield units), more typically at least 1000 HU or 1500 HU even more typically at least 2500 HU and particularly at least 4000 HU, when measured by microCT, at 65 kV, especially as measured according to Example 18. Polymers having a radio density of at least 45001 HU may be particularly useful in some embodiments.

Where the polymer is used to provide a liquid embolic, for example, it may be advantageous to use polymers having a radio density of at least 4500 HU, typically at least 5000 and more typically at least 6000 HU.

Liquid embolic compositions are compositions where the polymer is delivered to the desired site within the body as a liquid, but forms an embolus in a blood vessel in vivo, particularly where the polymer gels, solidifies or precipitates in situ to form the embolus. Typically the polymer is in the form of a solution of the polymer in a solvent. In one embodiment the polymer may form a hydrogel. A further aspect of the present disclosure provides liquid compositions comprising the PVA polymers described herein. These compositions are suitable as liquid embolic compositions. Thus the polymer may be in the form of a liquid embolic composition comprising a solvent that dissipates in the blood, thereby depositing the polymer within the blood vessel as an embolus.

A second aspect therefore provides a composition comprising a polymer according to the first aspect of the present disclosure, dissolved in a solvent. These compositions may be used in a number of approaches to medical treatment including, but not limited to, the provision of fiducial markers, drug depots, tissue spacing compositions and liquid embolics.

The solvent typically comprises an organic solvent. Beneficially the composition comprises the PVA polymer dissolved in the solvent to form a solution of the polymer in the solvent.

In one embodiment, the polymer precipitates from the composition or forms a gel, or gel-like embolus at the target site within the body. Precipitation or gelation of the polymer from the composition in phosphate buffered saline (PBS: NaCl 136.7 mM, KCl 2.7 mM, $Na_2HPO_4$ 10.1 mM, $KH_2PO_4$ 1.7 mM: pH7.4) at 20° C. may be used as a guide for this property, and so liquid (solution) compositions in which the polymer precipitates or gelates under these conditions (such as in a 500 fold volume excess of PBS) provide a further embodiment of the present disclosure. The radiodensity and iodine content of these precipitates/gels is within the ranges described for other embodiments of the present disclosure, but is typically as described above for liquid embolics. It is to be noted, however, that the embolus formed may comprise voids. The figures provided for radiodensities are for the polymer, rather than for an average across the embolus.

Typically the solvent used is a water miscible organic solvent. By water miscible is meant that 0.5 ml of the solvent is completely soluble in 1 litre of PBS at 20° C.

Typically these organic solvents are biocompatible. More typically, the solvents are biocompatible polar aprotic solvents, such as DMSO, DMF, DMPU (N, N-dimethylpropyleneurea), DMI (1,3-dimethyl-2-imidazolidinone), glycerol, ethyl lactate, NMP and glycofurol (2-(Oxolan-2-yl methoxy)ethanol). The solvents are even more typically selected from DMSO and NMP and particularly DMSO. In one embodiment, the solvent may comprise up to 25% w/v water, and beneficially up to 10%. In another embodiment, however, the solvent does not contain water.

Beneficially these compositions are provided as an injectable liquid composition. Such compositions are typically rheologically suitable to pass down a delivery catheter, particularly with manual pressure, however the catheter internal diameter will vary depending on the procedure, so the maximum viscosity level tolerated will be dependent on the catheter, procedure and delivery method. The viscosity is typically less than 600 cP at 24° C., particularly less than 400 cP. Such compositions provide good delivery characteristics.

Typically the liquid composition comprises 3 to 70% wt/wt, more typically 5 to 40% wt/wt and most typically 15 to 30% wt/wt of the polymer dissolved in the solvent.

Polymers used in liquid embolics are typically polyvinyl alcohol homopolymer or co-polymers. The PVA polymers used as liquid embolics, are typically not covalently cross-linked. Thus the PVA polymer is typically a PVA homopolymer or co-polymer, and more typically a PVA homopolymer, which is not covalently cross linked.

The native PVAs suitable for use in the present disclosure may be of any suitable molecular weight. Beneficially, though, they may have a weight average molecular weight ranging from 1 kDa to 250 kDa. For liquid embolics, the PVA has a weight average molecular weight of at least 3 kDa and typically at least 5 kDa. and more typically at least 10 kDa. Typically the weight average MW is less than or equal to 150 kDa, more typically less than or equal to 100 kDa, and even more typically less than or equal to 75 kDa. Typical ranges include 10 to 75 kDa, 10 to 50 kDa, 5 to 50 kDa and 25 to 75 kDa weight average molecular weight. Preparations of native PVA having a mixture of molecular weights in which the majority are 13 to 23 kDA and 31 to 50 kDa have been successfully used.

The radiopaque polymers described herein are useful generally in the preparation of implanted medical devices and such devices, comprising polymers described herein provide a further aspect of the present disclosure. Devices include, but are not limited to, microspheres, liquid embolics, fiducial markers, tissue-spacing materials, injectable bulking agents, sealants, depots in which the polymer additionally comprises an active agent and from which the active agent elutes into the surrounding tissue, wound dressings, and coatings for medical devices e.g. to render them visible under X-ray.

The polymers described herein may be used for the delivery of a variety of pharmaceutical actives. Compositions comprising a polymer as described herein and a pharmaceutical active are therefore a further aspect of the present disclosure.

Since such pharmaceutical actives are intended for local delivery, they are typically free to elute form the polymer in aqueous solutions. The pharmaceutical active may be bound to the polymer by electrostatic interactions, by association with a charged component of the polymer. non-limiting examples of such pharmaceutical actives include: camptothecins (such as irinotecan and topotecan) and anthracyclines (such as doxorubicin, daunorubicin, idarubicin and epirubicin), antiangiogenic agents (such as vascular endothelial growth factor receptor (VEGFR) inhibitors, such as axitinib, bortezomib, bosutinib canertinib, dovitinib, dasatinib, erlotinib gefitinib, imatinib, lapatinib, lestaurtinib, masutinib, mubitinib, pazopanib, pazopanib semaxanib, sorafenib, sunitinib, tandutinib, vandetanib, vatalanib and vismodegib), microtubule assembly inhibitors (such as vinblastine, vinorelbine and vincristine), Aromatase inhibitors (such as anastrazole), platinum drugs (such as cisplatin, oxaliplatin, carboplatin and miriplatin), and nucleoside analogues (such as 5-FU, cytarabine, fludarabine and gemcitabine). Other beneficial drugs include paclitaxel, docetaxel, mitomycin, mitoxantrone, bleomycin, pingyangmycin, abiraterone, amifostine, buserelin, degarelix, folinic acid, goserelin, lanreotide, lenalidomide, letrozole, leuprorelin, octreotide, tamoxifen, triptorelin, bendamustine, chlorambucil, dacarbazine, melphalan, procarbazine, temozolomide, rapamycin (and analogues, such as zotarolimus, everolimus, umirolimus and sirolimus), methotrexate, pemetrexed and raltitrexed.

A further aspect of the present disclosure provides methods of medical treatment comprising delivering a polymer as described herein, to a blood vessel of a subject in need thereof, such as to form an embolus. The polymer may be, for example, a microsphere or other particulate form or may be a liquid embolic comprising a polymer as described herein. processes for making microspheres are provided, for example, in WO 2004/071495 and WO 2015/033092.

Where the polymer is in the form of a liquid embolic, the polymer may be delivered in the form of a composition comprising a solvent that dissipates in the blood stream to provide an embolus, typically an organic solvent as described above.

In a further embodiment, the present disclosure also provides pharmaceutically active ingredients as described herein, for use in a method of medical treatment, wherein the treatment comprises delivering the pharmaceutical active to the patient in the form of an embolic composition comprising the pharmaceutical active as described herein and from which the pharmaceutical active is eluted during the treatment. The composition may, for example, comprise microspheres comprising the pharmaceutical active, or maybe a liquid embolic comprising the pharmaceutical active.

The microspheres and liquid embolics described herein may be used to treat a variety of conditions including arteriovenous malformations, gastrointestinal bleeding, filling of aneurysms, treatment of solid tumours, particularly hypervascular tumours, such as those of the liver, prostate, kidney, brain, colon, bone and lung. As well as benign hyperplastic conditions such as prostate hyperplasia or uterine fibroids. The approach can also be used in the treatment of obesity and joint pain.

General synthetic approaches are described below.

A radiopaque polymer in which pendant groups are coupled through an ester linkage, may be prepared by reacting the PVA polymer with compounds of the formula 5a 5b and 5c 5a

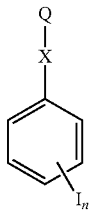

5b

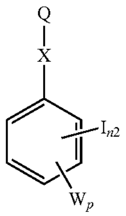

5c

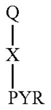

where Q is a carboxylic acid, an acid halide (such as —COCl or —COBr) or an activated carboxylic acid.

Where Q is a carboxylic acid, the reaction is typically carried out under acid conditions (e.g. sulphuric acid, trifluoroacetic acid, trifluoromethane sulphuric acid, hydrobromic acid in acetic acid, acetic acid & methanesulfonic acid, etc.) in an appropriate polar solvent (e.g. DMSO, DMF, NMP, etc.).

Where Q is an acid halide the reaction is typically carried out under mild basic conditions in an appropriate polar solvent (e.g. DMSO, DMF, NMP, etc.) for example in the presence of a mild base (e.g. pyridine, trimethylamine, lutidine, collidine, imidazole, etc.).

Where Q is an activated carboxylic acid, activating agents such as carbodiimides and carbodiidazoles e.g. DCC (N,N'-dicyclohexylcarbodiimide), EDCI (N-(3-dimethylamino-propyl)-N'-ethylcarbodiimide) and HOBt (hydroxybenzotrazole) may be used in polar aprotic solvents, such as DMSO, tetrahydrofuran, ethyl acetate, acetone, dimethylformamide and acetonitrile, among others. The reaction is typically carried out in the presence of a catalytic amount of a base and under anhydrous conditions to achieve activation. The base is typically of moderate strength (e.g., pKa of conjugate acid around 10-13) and suitable bases include a variety of pyridines, amines nitrogen heterocycles, triethylamines, N,N-diisopropylethylamine, DMAP and the like.

Coupling iodinated phenyl groups to a polyhydroxylated polymer via an ester linkage, is discussed and exemplified in WO2011/110589, WO2014/152488 and Mawad et al (2009) Biomaterials, 30, 5667-5674, for example.

For the formation of ether linkages, a PVA polymer may be reacted, for example, with a compound of the formula VI wherein Q is a group selected from halides, such as fluoride, chloride, bromide, or iodide, methylsulfonate, methyltoluenesulfonate and trifluoromethane-sulfonate. Q may be for example bromine.

Coupling iodinated phenyl groups to a polyhydroxylated polymer via an ether linkage, is discussed in WO2011/110589.

Coupling of pendant groups through a 1,3, dioxane may be prepared by reacting the polyhydroxylated polymer with a compound of the formula VI wherein Q is a group selected groups capable of forming a cyclic acetal with a 1,3-diol group, beneficially under acidic conditions. In this case Q is beneficially selected from the group consisting of aldehydes, acetals, and hemiacetals. Coupling iodinated groups to PVA in this manner, is described in WO2015/033092.

Any combination of coupling approach may be used to couple groups of the formula 5a and a second group of the formula 5b or 5c, i.e. groups Q may be independently selected in each case, however, in a particularly beneficial embodiment, the reaction is carried out on compounds of formula 5a, and 5b or 5c such that each pendant group is bound to the PVA backbone by the same coupling group. Each compound of the formula 5 may have the same or different Q groups, although Q groups may be varied in order to optimise the reaction. Each compound of the formula 5 may having the same Q group. It is convenient that the compound of the formula 5a and the compound of the formula 5b or 5c are coupled concurrently, in order to simplify the process.

In a particularly beneficial embodiment, a polymer is synthesised by reacting a polymer comprising PVA with a compound of the formula 5a 5a

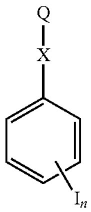

and with a compound of the formula 5b or 5c

5b

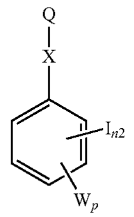

or

5c

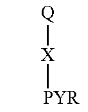

wherein, in each case independently, Q is selected from groups capable of forming a 1,3 dioxane group by reaction with a 1,3 diol group;

PYR is a pyridyl group;

X is as described elsewhere herein.

In this case Q is beneficially selected from the group consisting of aldehyde, acetal and hemiacetal groups, and particularly groups selected from —CHO, —$CHOR^{11}OR^{12}$—$CHOR^{13}OH$ Wherein $R^{11}$ $R^{12}$ and $R^{13}$ are independently in each case selected from $C_{1-4}$ alkyl; beneficially methyl or ethyl.

The reaction is beneficially carried out such that the compound of the formula 5a is reacted with the polymer concurrently with either compound 5b or 5c. The reaction is beneficially carried out under acidic conditions.

DETAILED DESCRIPTION OF PARTICULAR EMBODIMENTS

Figure 1A:
FIG. 1A shows a sample of a liquid embolic composition in PBS shortly after formation.

The present disclosure will now be described further by way of the following non-limiting examples with reference to the figures. These are provided for the purpose of illustration only and other examples falling within the scope of the claims will occur to those skilled in the art in the light of these. All references cited herein are incorporated by reference in their entirety. Any conflict between that reference and this application shall be governed by this application.

Example 1: Preparation of 2,3,5-triiodobenzaldehyde from 2,3,5-triiodobenzyl alcohol

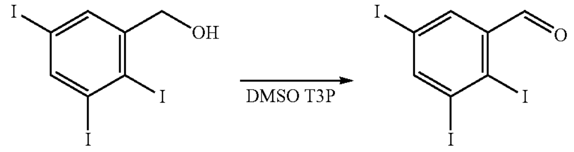

2,3,5-triiodobenzaldehyde may be prepared according to example 1 of WO2015/033092.

Example 2: Preparation of 2-(2,3,5-triiodophenoxy)acetaldehyde

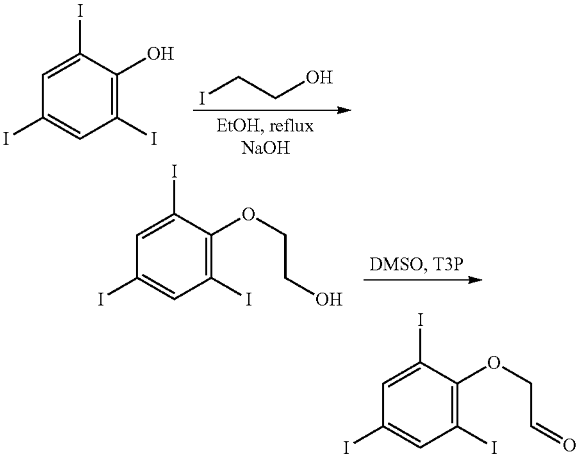

(a) Synthesis of 2-(2,4,6-triiodophenoxy)ethanol from 2,4,6-triiodophenol

This compound may be prepared according to example 2(a) of WO2015/033092.

(b) Oxidation of 2-(2,4,6-triiodophenoxy)ethanol to 2-(2,3,5-triiodophenoxy) acetaldehyde This compound may be prepared according to example 2(b) of WO2015/033092.

Example 3: Preparation of 1-(2,2-dimethoxyethoxymethyl)-2,3,5-triiodo-benzene from 2,3,5-triiodobenzyl alcohol and 2-bromo-1,1-dimethoxy-ethane (Example of a radiopaque acetal/protected aldehyde).

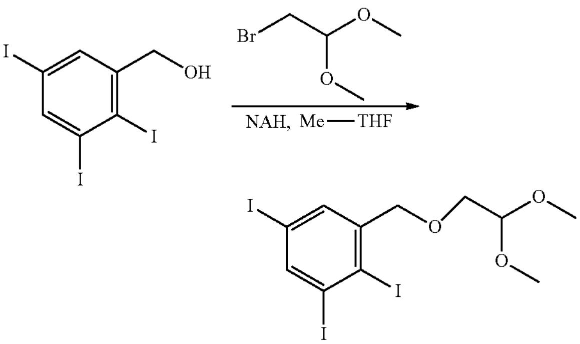

This compound may be prepared according to example 3 of WO2015/033092.

Example 4: Synthesis of 3,5-diiodo-2-(2-(2-methoxyethoxy)ethoxy)benzaldehyde.

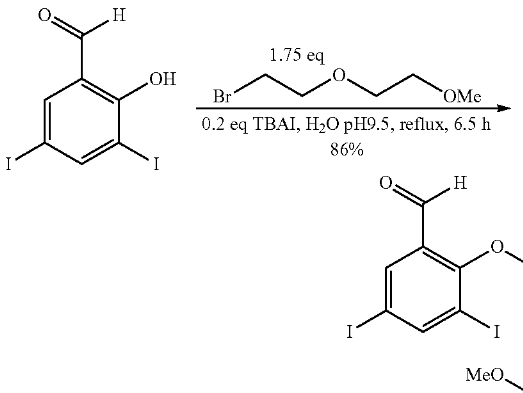

To a HEL PolyBlock8 parallel synthesis 125 ml reactor fitted with a reflux condenser and suspended magnetic stirrer, was added 3,5-diiodosalicylaldehyde (13.9011 g, 37.72 mmol, 1.0 eq) and TBAI (2.7481 mg, 0.802 mmol, 0.2 eq). To this was added water and the pH adjusted to 9.5 with 1M NaOH (total aqueous volume 97 ml). The reactor was set to 500 rpm stirring until full dissolution to give a bright yellow solution and 1-bromo-2-(2-methoxyethoxy)ethane (5.00 ml, 37.17 mmol, 1.0 eq) was added. The reactor zone was set to heat to 120° C.

The reaction was monitored by Thin Layer Chromatography (TLC) (30% EA in i-hex) and after 2 hours additional bromide was added (2.50 ml, 18.59 mmol, 0.5 eq). After a further 0.5 hours, the pH was readjusted to 9.5 due to consumption of the bromide. After a further 2 hours additional bromide (1.25 ml, 9.29 mmol, 0.25 eq) were added and the reactor temperature was lowered to 50° C. and left to stir overnight.

After 19 hours, the resulting suspension was reheated to reflux for 1 hour, cooled to room temperature and transferred to a separating funnel in ethyl acetate (400 ml). The organics were washed twice with saturated sodium bicarbonate, dried with magnesium sulfate, hot filtered from toluene, and recrystallised from toluene/isohexane to give, after filtration and hi-vacuum drying, the desired product as a yellow powder:

(15.2909 g, 86.4% yield); $\delta_H$ ($CDCl_3$, 500.1 MHz)/ppm; 10.31 (1H, s), 8.31 (1H, d, 2.2 Hz), 8.09 (1H, d, 2.2 Hz), 4.26 (2H, app. t, 4.5 Hz), 3.89 (2H, app. t, 4.5 Hz), 3.67 (2H, app. t, 4.6 Hz), 3.55 (2H, app. t, 4.6 Hz), 3.38 (3H, s); $\delta_C$ NMR ($CDCl_3$, 125.8 MHz)/ppm; 188.71 (CH), 161.55 (q), 152.43 (CH), 137.57 (CH), 131.75 (q), 94.07 (q), 89.19 (q), 75.56 (CH2), 71.90 (CH2), 70.79 (CH2), 70.06 (CH2), 59.13 (CH3).

Example 5: Synthesis of 3-Hydroxy-2,4,6-triiodobenzaldehyde.

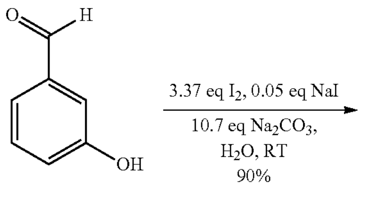

-continued

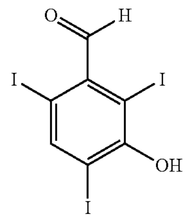

To a 2 L 3-necked round bottomed flask with large oval stirrer bar was added 3-hydroxybenzaldehyde (10.007 g, 81.89 mmol), sodium iodide (0.614 g, 4.09 mmol, 0.05 eq) and sodium carbonate (93.028 g, 877.44 mmol, 10.7 eq), rinsed in with a total of 750 ml of deionised water. When the benzaldehyde had dissolved to give a bright yellow stirred solution, iodine balls (70.008 g, 275.80 mmol, 3.37 eq) was added in 2 portions over 30 minutes and rinsed in with 225 ml of water each time. The reaction is followed by TLC (60% DCM in i-hex) and over 3 hours, the iodine almost completely dissolves resulting in a dark yellow/orange precipitate. The solid was isolated by Buchner filtration and washed with i-hexane to remove any residual iodine. The isolated solid was re-dissolved in warm water (2 L, 45° C.) to give a clear brown solution to which 100 ml of saturated sodium thiosulfate solution were added to reduce any remaining iodine. The pH of the solution was cautiously reduced from 10.2 to 3.26 using 1M HCl (with care taken due to evolution of $CO_2$). The solid was isolated by filtration, washed with water (2×500 ml) and dried in a high vacuum oven at 30° C. to give the desired compound as a yellow solid: (37.002 g, 90.3% yield, 97.2% HPLC purity); $\delta_H$ ($CDCl_3$, 500.1 MHz)/ppm; 9.65 (1H, s), 8.35 (1H, s), 6.42 (1H, s); $\delta_C$ NMR ($CDCl_3$, 125.8 MHz)/ppm; 194.90 (CH), 155.12 (q), 149.77 (CH), 135.69 (q), 88.78 (q), 87.66 (q), 85.70 (q).

Example 6: Synthesis of 2,4,6-triiodo-3-(2-(2-methoxyethoxy)ethoxy)benzaldehyde

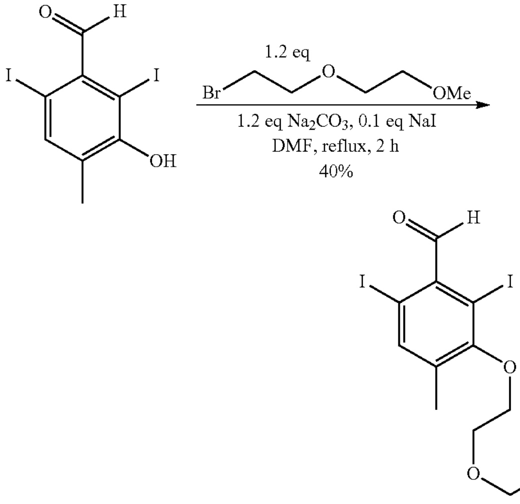

To a flame dried 250 ml 3-necked round bottomed flask under a nitrogen atmosphere containing a stir bar and fitted with a reflux condenser, were added 3-hydroxy-2,4,6-triiodobenzaldehyde (15.627 g, 31.3 mmol, 1.0 eq), sodium iodide (469 mg, 3.13 mmol, 0.1 eq), anhydrous sodium carbonate (3.981 g, 37.6 mmol, 1.2 eq) and anhydrous dimethylformamide (DMF) (160 ml).

The suspension was stirred until the aldehyde had completely dissolved, then 1-bromo-2-(2-methoxyethoxy)ethane (6.87 g, 37.5 mmol, 1.2 eq) was added by syringe and the reaction heated to reflux. After 2 hours, TLC analysis (10% EA in i-hex) indicated the start material was consumed and the reaction was cooled to room temperature, transferred to a 250 ml round bottomed flask and evaporated to dryness under high vacuum. The resulting suspension was diluted with 500 ml of ethyl acetate, washed with 3×100 ml 1M NaOH, 2×100 ml saturated brine, decolourised with activated charcoal and dried with magnesium sulfate. The resulting solution was concentrated to dryness, and purified by silica column chromatography (2-20% ethyl acetate in i-hexane) and dried under high vacuum to give the desired compound as a yellow powder:

(7.556 g, 40.1%); $\delta_H$ ($CDCl_3$, 500.1 MHz)/ppm; 9.65 (1H, s), 8.44 (1H, s), 4.20 (2H, t, 6.4 Hz), 4.01 (2H, t, 6.4 Hz), 3.79 (2H, app. t, 5.8 Hz), 3.60 (2H, app. t, 5.8H), 3.41 (3H, s); $\delta_C$ NMR ($CDCl_3$, 125.8 MHz)/ppm; 194.97 (CH), 159.10 (q), 150.83 (CH), 138.27 (q), 97.06 (q), 95.70 (q), 90.40 (q), 72.47 (CH2), 72.04 (CH2), 70.89 (CH2), 68.89 (CH2), 59.19 (CH3).

Example 7: Synthesis of 2,4,6-Triiodo-3-(2-(2-(2-methoxyethoxy)ethoxy)ethoxy)benz aldehyde.

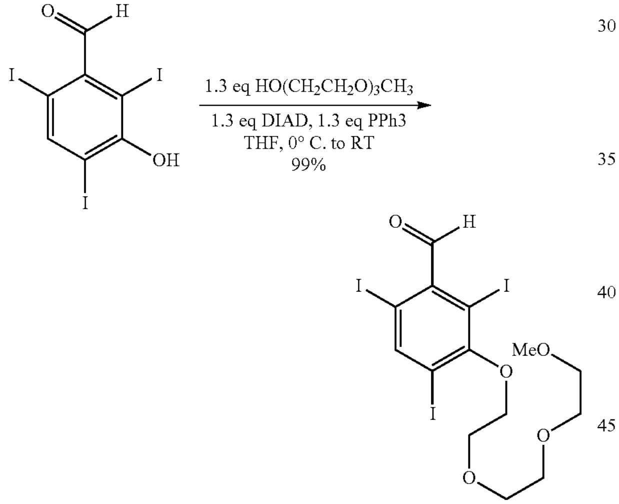

To a flame dried 100 ml 3-necked round bottomed flask containing a stirrer under a nitrogen blanket, was added triphenylphosphine (1.7216 g, 6.502 mmol, 1.3 eq) and anhydrous tetrahydrofuran (THF) (35 ml). The stirring was started and, after full dissolution of the triphenylphosphine (PPh3), the reactor was cooled to ca 0° C. in an ice-bath. To the colourless solution was added to Diisopropyl azodicarboxylate (DIAD) (1.28 ml, 6.502 mmol, 1.3 eq) dropwise via syringe resulting in a persistent yellow solution. After stirring for 5 minutes, triethylene glycol monomethyl ether (1.04 ml, 6.502 mmol, 1.3 eq) was added dropwise by syringe. After stirring for a further 5 minutes, the 3-hydroxy-2,4,6-triiodobenzaldehyde (2.5077 g, 5.002 mmol, 1.0 eq) was added in one portion resulting in an immediate colour change. The reaction was monitored by TLC (5% $Et_2O$ in toluene) and left to stir overnight. The solution was diluted with ether to precipitate triphenylphosphine oxide and then concentrated to dryness. The resulting thick oil was purified by column chromatography (2-10% $Et_2O$ in toluene) to give, after concentration and high vacuum drying, the desired product as a yellow powder: (3.2077 g, 99% yield, 94.4% HPLC purity); $\delta_H$ (DMSO-$D_6$, 500.1 MHz)/ppm; 9.58 (1H, s), 8.47 (1H, s), 4.08 (2H, t, 4.9 Hz), 3.57-3.53 (4H, m), 3.44 (2H, app. t, 4.8 Hz), 3.24 (3H, s).

Example 8: Synthesis of 3,4,5-Triiodosalicylaldehyde

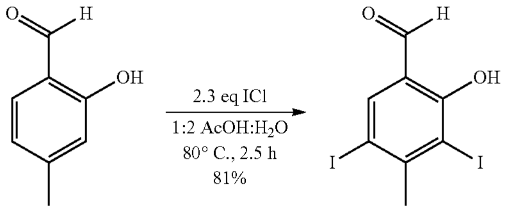

To a 3-necked 2 L round bottomed flask containing a large oval stirrer was added 4-iodo-salicilaldehyde (25.01 g, 100.86 mmol, 1.0 eq) and acetic acid (300 ml). After stirring for 5 minutes to allow the solid to dissolve, pre-warmed liquid iodine monochloride (39.11 g, 2.4 eq) was diluted with AcOH (100 ml) and transferred to a dropping funnel on the round bottomed flask. This solution was added over 10 minutes.

The reactor was then placed in a large silicone oil batch a fitted with a 1 L dropping funnel, thermometer and condenser and set to heat to 80° C. During the heat up, water (700 ml) was slowly added to the solution causing a yellow/orange precipitation. After 20 mins at 80° C., the heating was turned off After a further 30 minutes the heating bath was removed and the black solution/yellow suspension allowed to cool to room temperature and stirred for 65 hours; the reaction was analysed by TLC (20% EA in iHex). The solid was isolated by Buchner filtration and washed with water (2×500 ml). To remove residual iodine crystals, the solid was repeatedly re-slurried with i-hexane (200 ml) until the i-hexane supernatant was no longer purple. The isolated solid was dried in a high-vacuum oven overnight to give the desired product as a yellow crystalline solid (40.84 g, 81% yield, 93.2% pure by HPLC analysis).

The product could be further recrystallised to higher purity from acetone:water (9:1):

$\delta_H$ ($CDCl_3$, 500.1 MHz)/ppm; 12.15 (1H, s), 9.67 (1H, s), 8.09 (1H, s); $\delta_C$ NMR ($CDCl_3$, 125.8 MHz)/ppm; 194.53 (CH), 159.58 (C), 142.24 (CH), 133.39 (C), 120.87 (C), 101.68 (C), 94.02 (C).

Example 9: Synthesis of 3,4,5-Triiodo-2-(2-(2-methoxyethoxy)ethoxy)benz-aldehyde

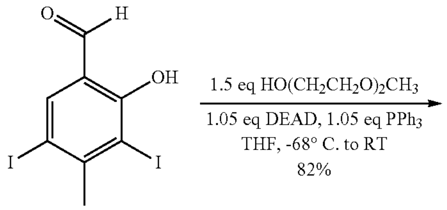

-continued

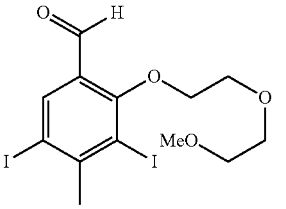

(5 g scale): To a flame dried 3-necked 250 ml round bottomed flask containing a small octagonal stirrer bar under a positive pressure of nitrogen, was added triphenylphosphine (2.76 g, 10.5 mmol, 1.05 eq) and dry THE (70 ml) by syringe. The round bottomed flask was placed in a Dewer bath fitted with a low temperature thermometer and cooled to −68° C. with an ethanol/liquid nitrogen bath. Diethyl azodicarboxylate (1.65 ml, 10.5 mmol, 1.05 eq) was added dropwise by syringe over 1 minute and left to stir for 5 minutes to give a yellow suspension. Diethyleneglycol mono-methyl ether (1.77 ml, 15 mmol, 1.5 eq) was then added dropwise and left to stir for 5 minutes. To this was added solid 3,4,5-triiodosalicylaldehyde (5.00 g, 10.0 mmol, 1.0 eq) in one portion. The initial dark orange/red suspension lightened to give a pale yellow solution which was allowed to stir for 2 hours, monitored by TLC analysis (20% ether in toluene) and left to warm up to room temperature overnight. TLC indicated complete consumption of aldehyde starting material with a clean reaction profile. The resulting solution was transferred to a 500 ml round bottomed flask, diluted with ether (200 ml) and cooled in the freezer. The resulting suspension was filtered through a short silica plug to remove triphenylphosphine oxide and flushed with further ether (200 ml). The resulting solution was concentrated to dryness, and purified by column chromatography eluting with ether in toluene (2-20%) with product fractions concentrated to dryness and dried under high vacuum to give the desired product as a yellow amorphous solid (4.91 g, 82% yield, 96% HPLC purity); $\delta_H$ ($CDCl_3$, 500.1 MHz)/ppm; 10.26 (1H, s), 8.34 (1H, s), 4.22 (2H, t, 4.5 Hz), 3.90 (2H, t, 4.5 Hz), 3.90 (2H, t, 4.6 Hz), 3.55 (2H, t, 4.6 Hz), 3.38 (3H, s); $\delta_C$ NMR ($CDCl_3$, 125.8 MHz)/ppm.

Example 10: Synthesis of 5-((2,2-Dimethoxyethyl)amino)-2,4,6-triiodoisophthalic acid.

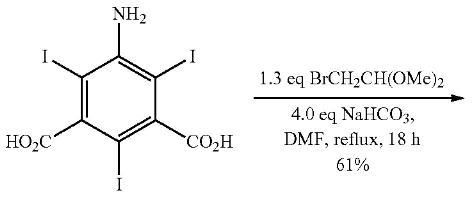

-continued

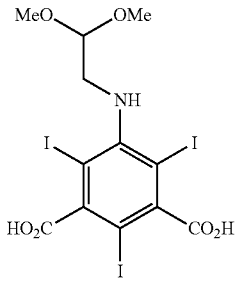

To a flame dried 500 ml round bottomed flask under nitrogen, was added solid 5-amino-2,4,6-triiodoisophthalic acid (46.95 g, 84.03 mmol, 1.0 eq), sodium bicarbonate (28.21 g, 335.8 mmol, 4.0 eq) and DMF (ca 400 ml) via cannula. To the resulting brown solution was added 2-bromo-1,1-dimethoxyethane (13 ml, 110.0 mmol, 1.3 eq) dropwise and the resulting solution heated to reflux for 18 hours. After cooling to room temperature, the majority of DMF was removed by rotary evaporation under vacuum (9 mBar, 55° C.) and the resulting orange solid extracted with ethyl acetate (1 L).

This suspension was washed with saturated lithium chloride solution (7×400 ml) to remove residual DMF and salts, dried over magnesium sulfate, filtered and evaporated to dryness. The resulting solid was recrystallised from ethyl acetate, washed with i-hexane and filtered. This process was repeated a total of 3 times and the resulting orange solid dried under high vacuum to give the title compound (33.04 g, 61%, 91.7% HPLC purity).

The product could be further purified via silica gel column chromatography (MeOH in DCM, 0-15%) (4.91 g, 82% yield, 96% HPLC purity); $\delta_H$ ($CDCl_3$, 500.1 MHz)/ppm; 8.01 (1H, s), 4.86 (2H, br s), 4.76 (1H, t, 5.5 Hz), 4.37 (2H, d, 5.5 Hz), 3.44 (6H, s); $\delta_C$ NMR ($CDCl_3$, 125.8 MHz)/ppm.

Example 11: Synthesis of Potassium 3-(3-formyl-2,4,6-triiodophenoxy) propane-l-sulfonate and 3-(1-formyl-3,4,5-triiodophenoxy)propane-1-sulfonate, sodium salt

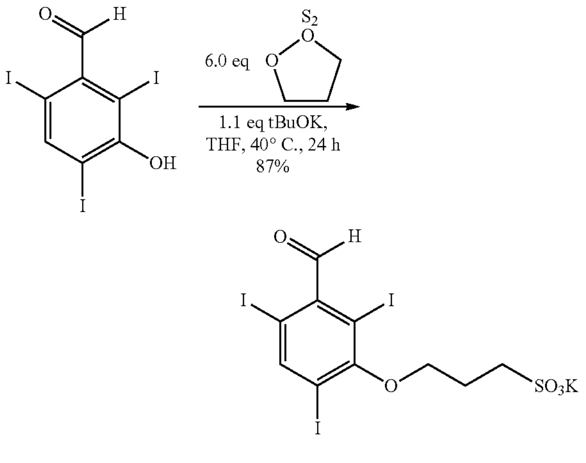

In a 150 mL three-neck round bottom flask, 3-hydroxy-2,4,6-triiodobenzaldehyde (10 g, 20 mmol, 1.0 eq) was dissolved in anhydrous THF(50 ml) by magnetic stirrer. Potassium t-butoxide (2.47 g 22 mmol, 1.1 eq) was mixed with 20 mL of THE and the suspension was added slowly into the flask under nitrogen atmosphere at room temperature, followed by increasing temperature to 40° C. to allow a full dissolution of product. Then sultone (15 g, 120 mmol, 6.0 eq) of was dissolved in 15 mL of THF and the mixture was added slowly to the reaction flask. A precipitation appeared almost immediately. After 3 hours reaction at 40° C., the reaction mixture was poured into 500 mL of ethyl acetate to receive solid raw product. The filtered solid was washed with 100 mL of ethyl acetate, and recrystallized from ethanol. After vacuum drying over 24 hours, the desired product (10.7 g, 80% yield,) was isolated; $\delta_H$ ($D_2O$, 500.1 MHz)/ppm; 2.24-2.34 (m, 2H), 3.12-3.25 (t, 2H), 3.88-4.02 (t, 2H), 8.18-8.25 (s, 1H), 9.42-9.50 (s, 1H) $\delta_C$ NMR ($CDCl_3$, 125.8 MHz)/ppm; Element analysis result: C, 18.56, H, 2.22, S, 5.66, I, 52.31, K, 6.27. Cal: C, 18.20, H, 1.22, S, 4.85, I, 57.68, K, 5.92.

3-(1-formyl-3,4,5-triiodophenoxy)propane-1-sulfonate, sodium salt was synthesized analogously from 3,4,5-triiodosalicylaldehyde (see example 8).

Example 12: General Coupling Conditions

To a pre-dried reactor under a nitrogen blanket is added PVA (typically 5-10 g) and anhydrous solvent (typically DMSO or NMP, 40 vol with respect to (w.r.t.) PVA mass) and catalyst (typically 2.2 vol w.r.t. PVA mass). The stirred suspension is heated to elevated temperature (ca 90° C.) to dissolve the PVA. When a homogeneous solution had been obtained, the mixture is cooled to the desired reaction temperature (typically 50-80° C.) the desired aldehyde substrate for the first and second pendant groups (typically 0.01 to 0.6 eq w.r.t. PVA diol functionalities) are added. The actual ratio of first and second pendant group aldehyde substrate to PVA 1,3-diol groups, and the ratio of first to second pendant groups, will depend on the tuning of hydrophilic to hydrophobic nature of the polymer required, but typically the first pendant group will be at a higher ratio than the second.

The reaction is then stirred under an $N_2$ blanket and the reaction conversion is monitored by HPLC for consumption of substrate. At a pre-determined time (typically when consumption of the substrate has ceased) an anti-solvent is added (typically, acetone, DCM, MeCN or TBME, ca 40 vol) dropwise from a dropping funnel.

The supernatant fluid is removed by aspiration through a filter membrane and further reaction solvent (typically 40 vol) is charged and stirred until the solids had fully dissolved. This solvent washing stage is repeated up to 3 times. Then the solid is re-dissolved in reaction solvent, and precipitated by the slow addition of water (typically up to 100 vol).

The resulting aggregated solid is removed from the supernatant and homogenised in a blender in water. The suspension is filtered and re-suspended in water (typically 100 vol), slurried for up to 30 minutes and filtered. The water slurrying is repeated until pH neutral had been obtained, then the damp solids are slurried in acetone (100 vol, 30 mins stir, 2 repetitions), filtered and dried in a high vacuum oven at 30° C. for up to 24 hours.

Example 13: Preparation of PVA Polymers Having a First Iodinated Pendant Group and a Second Non Iodinated Pendant Group on the Same PVA Backbone The following polymers were prepared:

First Pendant Group:

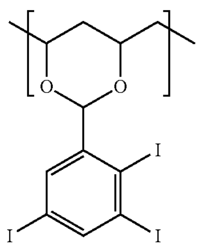

| | (a) | (b) | (c) | (d) |
|---|---|---|---|---|
| Second Pendant Group | 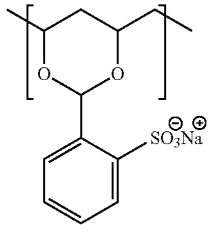 | 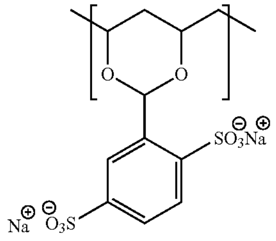 | 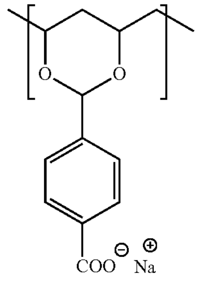 | 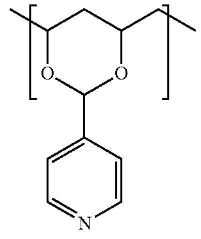 |

A dry 600 ml HEL Ltd PolyBLOCK® vessel (Borehamwood WD6 1GW, United Kingdom) was purged with nitrogen and provided with a nitrogen blanket. Dry DMSO (120 ml, 40.2 vol) was added with stirring at 500 rpm, followed by PVA (146-189 kDa, 99% hydrolysed, 5.0 g). The suspension was heated to 50° C. (internal probe) until all solids were completely dissolved. 1, 3, 5-triiodobenzaldehyde (TIBA) was then added (10.4 g, 0.4 eq w.r.t. PVA-1,3-diol units) followed by 0.05 eq of either:

(a) 2-sulfobenzaldehyde sodium salt, (Sigma Aldrich UK) (FSAS)
(b) 4-formylbenzene 1,3 disulfonic acid disodium-salt, (Sigma Aldrich UK) (D-FSAS)
(c) 4-formylbenzoic acid (Sigma Aldrich UK) (FBAS); or
(d) 4-pyridinecarboxyaldehyde (Sigma Aldrich UK) (Pyr)

After full dissolution, methanesulfonic acid (11 ml, 3.37 vol), diluted with ~20 mL of cold DMSO and added and stirring continued overnight at 50° C. The pale-yellow solution was cooled to room temperature and transferred into 1 L glass breaker containing a large stirrer bar. Acetonitrile (250 mL) was then added from a dropping funnel to precipitate the product.

The yellow supernatant was removed by vacuum and the resulting white polymer slowly re-dissolved in a minimum amount of DMSO (~100 ml) at 50° C. and re-precipitated with acetonitrile. Excess solvent was removed by vacuum. The white polymer was suspended in NaOH 0.1N solution (100 mL) for 20 min, then gently blended to achieve a homogeneous suspension that was carefully neutralised with deionised water (100×3) until pH=7 after removal of the excess solvent. The obtained white polymer was suspended in acetone (100 mL×3) after removing excess water by vacuum and the solid isolated by filtration, using a Buchner funnel. The solid was then dried in a vacuum oven at 28-32° C. overnight to give the desired product (white solid 11-13.0 g, ~75-80% w/w yield). Table 2 gives the elemental analysis of a selection of these polymers.

Figure 1B:
FIG. 1B shows a second sample ($PVA_{(146-186\ kDa)}$-$TIBA_{(0.4eq)}$-D-$FSAS_{(0.2eq)}$) shortly after formation.
Figure 1C:
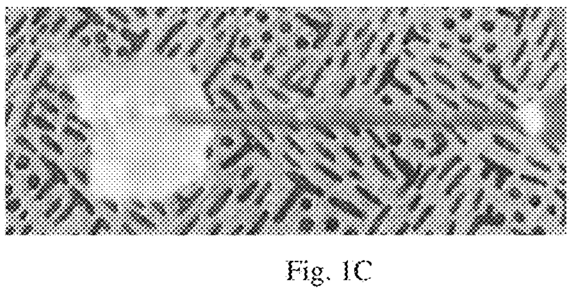
FIG. 1C shows a mature plug of liquid embolic material following dissipation of DMSO.

A 20% (w/w) solution in DMSO, of each polymer, was prepared. The solutions were injected into PBS and quickly gelled and solidified as the DMSO dissipated in the water. An example is shown in FIGS. 1A-1C.

TABLE 2

| Sample | C | H | N | S | I | Na |
|---|---|---|---|---|---|---|
| PVA(146-186 KDa) TIBA(0.4) FBASS(0.2) | 32.46 | 3.11 | <0.1 | <0.1 | 47.61 | 1.26 |
| PVA(146-186 KDa) TIBA(0.4) Pyr (0.2) | 30.72 | 3.02 | 0.68 | <0.1 | 53.98 | <0.01 |

TABLE 2-continued

| Sample | C | H | N | S | I | Na |
|---|---|---|---|---|---|---|
| PVA(146-186 KDa) TIBA(0.4) D-FSAS(0.2) | 37.84 | 2.91 | <0.1 | 3.34 | 46.23 | 2.02 |

Example 14: Preparation of PVA Polymers Having a First Iodinated Pendant Group and a Second Iodinated Pendant Group on the Same PVA Backbone The following polymers were prepared:

First Pendant Group:

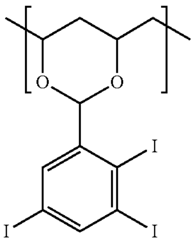

| | (a) | (b) |
|---|---|---|
| Second pendant group: | 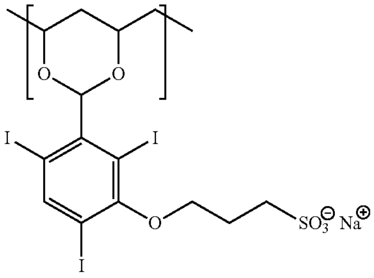 | 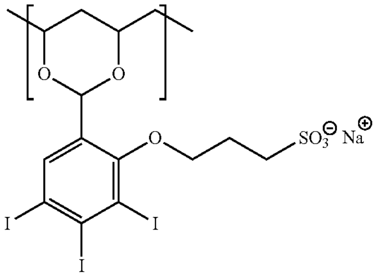 |

To a dry 50 ml HEL Ltd PolyBLOCK© vessel degassed, purged with nitrogen and provided of a nitrogen blanket, dry DMSO (20 ml) was added stirring at 500 rpm. Then PVA (13-23 kDa, 99% hydrolysed, 1.0 g) was added heating to 65° C. (internal probe) stirring at 500 rpm until all the solids was completely dissolved. After this time, TIBA, 2.2 g, 0.4 eq w.r.t. PVA-1,3-diol units) followed by either:

a. 3-(3-formyl-2,4,6-triiodophenoxy)propane-1-sulfonate, sodium salt; or
b. 3-(1-formyl-3,4,5-triiodophenoxy)propane-1-sulfonate, sodium salt, at (0.1 eq w.r.t PVA-1,3-diol units). After full dissolution, methanesulfonic acid (2.2 ml) was added dropwise stirring the reaction at 65° C. overnight. The orange solution was cooled to room temperature and poured dropwise in to 500 mL glass breaker containing acetone 200 mL. A white solid was recovered and re-dissolved in DMSO 50 mL and precipitated again in acetone 500 mL. The solid was collected on a Buchner funnel and the excess of acid neutralised with 0.1N NaOH solution (~100 mL) washing with deionised water until a neutral pH was achieved. The solid was then dried in a hi-vacuum oven at 28-32° C. overnight to give the desired product as off-white solid (3.0 g, ~70% w/w yield). A 20% (w/w) solution in DMSO, of each polymer, was prepared.

Example 15: General Preparation of Liquid Embolic Prototypes

A sample prototype is prepared in the following fashion: iodinated PVA prepared according to the above examples, is weighed into a 10 ml vial, to which is added the desired solvent (typically DMSO or NMP) such that the overall concentration is in the range 4-20% w/w with a total volume being less than 10 ml. The vial containing the thick suspension is then sealed, placed in a sonicator and sonicated until complete dissolution had occurred (typically ca. 4 hours).

Example 16: Precipitation of Liquid Embolic Under Flow Conditions

A clear detachable tube was attached to a flow system through which PBS (Biosciences, UK) was pumped using a peristaltic pump to mimic blood flow conditions. A 2.4 Fr catheter was used to deliver the liquid embolic preparation into the detachable tube. As the liquid embolic leaves the catheter and comes into contact with PBS, it is precipitated or gelled inside the detachable tubing. Observations on the length, and other characteristics of the precipitated/gelled polymer where then recorded. Flow rate and rate reduction are also recorded. The "longest length of advancement" is recorded. If reflux of the embolus occurs, its length is also recorded as the "longest length of reflux" (cm).

TABLE 3

| Sample | Conc. (%, w/w) | Viscosity @ 24 °C (cP) | Longest length of advance (cm) | Longest length of reflux (cm) | Embolization efficiency | Observation |
|---|---|---|---|---|---|---|
| $PVA_{13kDa}$-$TIBA_{0.4eq}$-$FSAS_{0.01eq}$ | 20.0% | 103.0 | 7.1 | 3.2 | 96.2% | Stringing at first, then lava like flow*. Embolisation further away from catheter. Opaque plug. |
| $PVA_{31kDa}$-$TIBA_{0.6eq}$-$FSAS_{0.1eq}$ | 27.5% | 1517.0 | 4.9 | 1.0 | 100.0% | Lava like flow, gel like plug. Injection resistance high. Transparent plug. |
| $PVA_{31kDa}$-$TIBA_{0.4eq}$-$FSAS_{0.1eq}$ | 20.0% | 297.0 | 5.5 | 1.7 | >98% | Stringing at first, then lava like Flow. Transparent gel plug. |
| $PVA_{13kDa}$-$TIBA_{0.6eq}$-$FSAS_{0.1eq}$ | 20.0% | 109.0 | 2.9 | 3.0 | 100.0% | Weak gel, formed string. No lava like flow. Transparent gel plug. |

*In lava-like flow, the embolic composition initially forms a slight crust on the surface, which inhibits stringing. The crust fractures as the embolic advances and the reforms on the advancing portion, and so on.

Example 17: X-Ray Analysis of Precipitated Liquid Embolic Samples

In order to obtain radiopacity measurements for the material, 1 cm sections of precipitated formulations are cut and embedded in warm (55° C.) 1% agarose in a polypropylene capped tube, (Nunc cryotube vials—Sigma-Aldrich product code V7634, 48 mm×12.5 mm) and scanned using Micro-CT according to the following protocol:

Samples were tested for radiopacity using micro-Computer Tomography (Micro-CT) using a Bruker Skyscan 1172 Micro-CT scanner at the RSSL Laboratories, Reading, Berkshire, UK, fitted with a tungsten anode. Each sample was analysed using the same instrument configuration with a tungsten anode operating at a voltage of 64 kV and a current of 155 μA. An aluminium filter (500 μm) was used. A two part analysis method is used. Initially an interpolated region of interest is created coving the inner tube diameter to include the plug and any void structures then the image is segmented to isolate the polymer from the void structures so as to report only polymer radiodensity. The radiodensity in HU was then calculated using the water standard acquired on the same day. Table 4 gives the acquisition parameters.

TABLE 4

| | |
|---|---|
| Software: | SkyScan1172 Version 1.5 (build 14) NRecon version 1.6.9.6 |
| CT Analyser version | 1.13.1.1 |
| Source Type: | 10 Mp Hamamatsu 100/250 |
| Camera Resolution (pixel): | 4000 x 2096 |
| Camera Binning: | 1 x 1 |
| Source Voltage | 65 kV |
| Source Current uA | 153 |
| Image Pixel Size (um): | 3.96 |
| Filter | Al 0.5 mm |
| Rotation Step (deg) | 0.280 |
| Output Format | 8bit BMP |
| Dynamic Range | 0.000-0.140 |
| Smoothing | 0 |
| Beam Hardening | 0 |

TABLE 4-continued

| | |
|---|---|
| Post Alignment | corrected |
| Ring Artefacts | 16 |

Figure 2A:
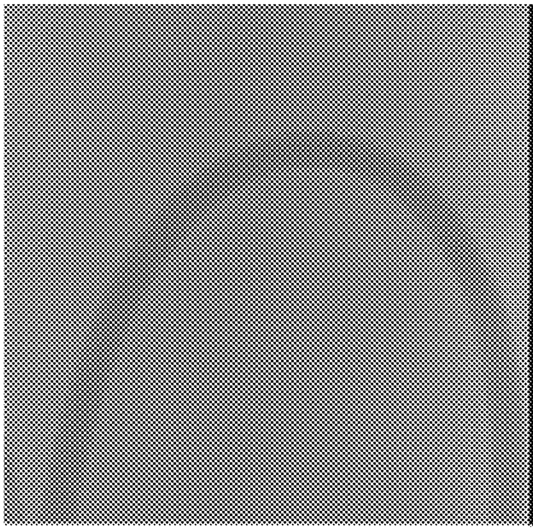
FIGS. 2A-2B show an X-ray shadow graph (FIG. 2A), and a reconstructed and segmented 2D cross-section (FIG. 2B) of a sample of a liquid embolic composition with the following composition: 20% PVA(13 kDa)-TIBA(0.4 eq)-FSAS(0.01 eq).
Figure 2B:
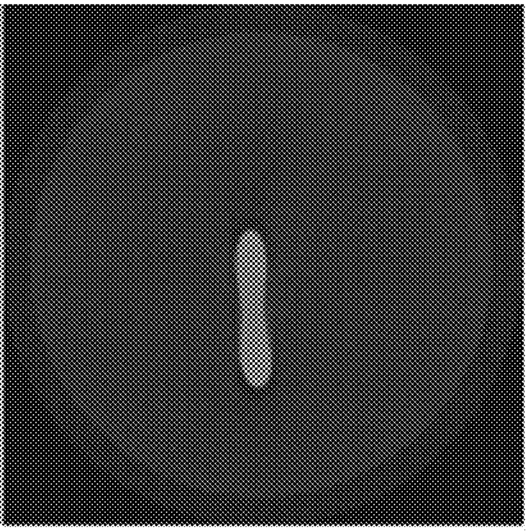

A small amount of purified MilliQ® water was carefully decanted into each sample tube. Each sample was then analysed by X-Ray micro-computer tomography using a single scan, to include the water reference and the sample (one such scan is shown in FIG. 2A). The samples were then reconstructed using NRecon and calibrated against a volume of interest (VOI) of the purified water reference (see FIG. 2B). A region of interest (ROI) of air and water was analysed after calibration to verify the Hounsfield calibration.

Radiodensity was reported in Hounsfield units. Values used for dynamic range for all samples in NRecon (thresholding): −0.005, 0.13 (minimum and maximum attenuation coefficient).

A polymer having the following composition: PVA(13 kDa)-TIBA(0.4 eq)-FSAS(0.01 eq) was dissolved in DMSO (20% w/w) and sealed inside a 0.58 mm polyethylene tubing for by microCT test (the tubing was embedded in agarose gel). The measured radiodensity was 6752 HU and the calculated iodine content of the solution is around 140 mg I/mL. Radiodensity figures for samples of liquid embolic compositions are given in Table 5.

Example 18. Viscosity Measurement

The viscosity of liquid embolics compositions prepared according to the above examples was measured using an Anton-Paar MCR 302 rheometer with 60 mm cone geometry. The temperature sweep was in the range of 20-40° C. and constant sear rate 5.0 $s^{-1}$ was applied. Sample results at 24° C. are given in Table 5 below.

Example 19: Water Content

The water content of the polymer was measured by dropping 1 mL of polymer DMSO solution into PBS to form rough spheres of a size of about 3-5 mm in diameter. After equilibrating in 500 mL of fresh PBS for 24 hr, the spheres were wicked dry with tissue to remove surface water and the weights were measured. The spheres were then dried in a vacuum oven over night at 50° C. The water content is expressed as percent by weight water, see Table 5.

TABLE 5

| | Iodine content in solid (w/w %) | TIBA/FSAS Molar ratio, Actual (calculated) | Conc. of DMSO solution (w/w) % | Radiopacity (HU) | Viscosity @ 24 ° C (cP) | Hydrogel water content at equilibrium (%) |
|---|---|---|---|---|---|---|
| $PVA_{13kDa}$-$TIBA_{0.4eq}$-$FSAS_{0.05eq}$ | 53% | 5.6 (8.0) | 25.0% | 7388 | 289.7 | 71.1 ± 0.6 |
| $PVA_{31kDa}$-$TIBA_{0.6eq}$-$FSAS_{0.1eq}$ | 57% | 4.5 (6.0) | 27.5% | 8697 | 1517.0 | 62.2 ± 0.2 |
| $PVA_{31kDa}$-$TIBA_{0.4eq}$-$FSAS_{0.1eq}$ | 52% | 2.7 (4.0) | 20.0% | 6597 | 297.0 | 73.9 ± 0.2 |
| $PVA_{13kDa}$-$TIBA_{0.6eq}$-$FSAS_{0.1eq}$ | 61% | 3.6 (6.0) | 20.0% | 7011 | 109.0 | 68.8 ± 1.8 |

The invention claimed is:

1. An implantable medical device comprising a polymer that comprises polyvinyl alcohol (PVA), the PVA having a first pendant group and a second pendant group, wherein the first pendant group comprises a first phenyl group bearing 1 to 5 iodines as the sole substituent(s) of the first phenyl group, and wherein the second pendant group comprises a group selected from:

(a) a second phenyl group bearing 1 to 3 substituents selected from the group W and optionally 1 to 4 iodine substituents, the group(s) W and the optional iodines being the sole substituents of the second phenyl group;

wherein each W is independently selected from —OH, —COOH, —$SO_3H$, —$OPO_3H_2$, —O—($C_{1-4}$alkyl), —O—($C_{1-4}$alkyl)OH, —O—($C_{1-4}$alkyl)$R^2$, —O—$(C_2H_4O)_qR^1$, —(C═O)—O—$C_{1-4}$alkyl and —O—(C═O)$C_{1-4}$alkyl; wherein $R^1$ is H or $C_{1-4}$ alkyl; $R^2$ is —COOH, —$SO_3H$, or —$OPO_3H_2$; wherein q is an integer from 1 to 4; and wherein the group W may be in the form of a pharmaceutically acceptable salt; and (b) a pyridyl group; which is optionally in the form of a pyridinium ion.

2. A medical device according to claim 1, wherein the first pendant group is coupled to the PVA through an ether, ester, amide or 1,3 dioxane group.

3. A medical device according to claim 1, wherein the second pendant group is coupled to the PVA through an ether, ester, amide or 1,3 dioxane group.

4. A medical device according to claim 1, wherein the first pendant group is a group according to formula 1A or 1B

1A

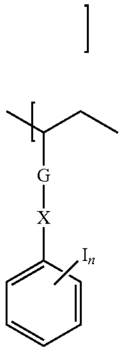

1B

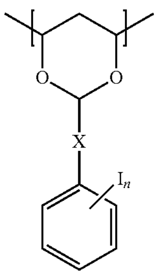

wherein

G is a coupling group through which the group of the formula 1A is coupled to the PVA and is selected from ether, ester and amide;

X is independently either a bond or is a linking group having a chain of 1 to 6 atoms selected from C, N, S and O, directly between the phenyl group and the coupling group, provided that the chain contains no more than one atom selected from N, S and O; wherein C is optionally substituted by a group selected from $C_{1-4}$ alkyl; wherein N is substituted by $R^3$, wherein $R^3$ is selected from H and $C_{1-4}$ alkyl; and wherein S is either an —S(O)— or —$S(O)_2$— group; and n is an integer from 1 to 5.

5. A medical device according to claim 1, wherein the second pendant group is of the formula 2A, 2B, 2C or 2D

2A

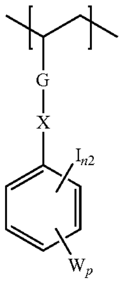

2B

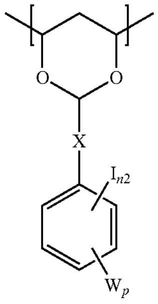

2C

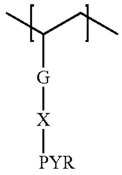

2D

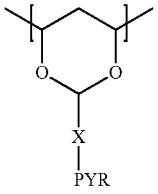

wherein

X is independently either a bond or is a linking group having a chain of 1 to 6 atoms selected from C, N, S and O, directly between the phenyl group and the coupling group, provided that the chain contains no more than one atom selected from N, S and O; wherein C is optionally substituted by a group selected from $C_{1-4}$ alkyl; wherein N is substituted by $R^3$, wherein $R^3$ is selected from H and $C_{1-4}$ alkyl; and wherein S is either an —S(O)— or —$S(O)_2$— group;

G is a coupling group through which the group of the formula 2A or 2C is coupled to the polyvinyl alcohol and is selected from ether, ester and amide;

W is independently selected from —OH, —COOH, —$SO_3H$, —$OPO_3H_2$, —O—($C_{1-4}$alkyl), —O—

($C_{1-4}$alkyl)OH, —O—($C_{1-4}$alkyl)$R^2$, —O—$(C_2H_4O)_q$ $R^1$, —(C═O)—O—$C_{1-4}$alkyl and —O—(C═O)$C_{1-4}$ alkyl;

wherein $R^1$ is H or $C_{1-4}$ alkyl; $R^2$ is —COOH, —$SO_3H$, or —$OPO_3H_2$; wherein q is an integer from 1 to 4; and wherein the group W may be in the form of a pharmaceutically acceptable salt; and PYR is a pyridyl group;

n2 is an integer from 0 to 4;

p is an integer from 1 to 3; and n2+p is an integer from 1 to 5.

6. A medical device according to claim 4 wherein X is selected from the group consisting of a bond, $C_{1-6}$alkylene groups; $C_{1-5}$ alkoxylene groups, groups of the formula —$(CH_2)_y$—O—$(CH_2)_z$— wherein y and z are, independently, 1, 2 or 3, and y+z is an integer from 2 to 5; and groups of the formula —N($R^3$)$(CH_2)_{n3}$— wherein $R^3$ is H or $C_{1-4}$ alkyl.

7. A medical device according to claim 4 wherein X is selected from the group consisting of a bond, methylene, ethylene, oxymethylene and oxyethylene, —$CH_2$—O—$CH_2$— and —NH($CH_2$)—.

8. A medical device according claim 1 wherein W is, independently in each case, selected from —OH, —COOH, —$SO_3H$, —O—($C_{1-4}$alkyl), —O—($C_{1-4}$alkyl)OH, —O—($C_{1-4}$alkyl)$R^2$, —O—$(C_2H_4O)_q R^1$, —(C═O)—O—$C_{1-4}$alkyl and —O—(C═O)$C_{1-4}$alkyl, wherein $R^1$ is H or $C_{1-4}$ alkyl; and $R^2$ is —COOH, or —$SO_3H$, and q is an integer from 1 to 4.

9. A medical device according to claim 1 wherein W is, independently in each case, selected from —OH, —COOH, —$SO_3H$, —O—($C_{1-4}$alkyl)$R^2$ and —O—$(C_2H_4O)_q R^1$; wherein $R^1$ is H or $C_{1-4}$ alkyl; $R^2$ is —COOH or —$SO_3H$; and q is an integer from 1 to 4.

10. A medical device according to claim 1, wherein W is, independently in each case, selected from —$SO_3H$ and —O—($C_{1-4}$alkyl)$R^2$; wherein $R^2$ is —$SO_3H$.

11. An implantable medical device comprising a polymer that comprises polyvinyl alcohol (PVA), the PVA having a first pendant group and a second pendant group, wherein the first pendant group comprises a first phenyl group bearing 1 to 5 iodines as the sole substituent(s) of the first phenyl group;

wherein the second pendant group comprises a group selected from:

(a) a second phenyl group bearing 1 to 3 substituents selected from the group W and optionally 1 to 4 iodine substituents, the group(s) W and the optional iodines being the sole substituents of the second phenyl group;

wherein each W is independently selected from —OH, —COOH, —$SO_3H$, —$OPO_3H_2$, —O—($C_{1-4}$alkyl), —O—($C_{1-4}$alkyl)OH, —O—($C_{1-4}$alkyl)$R^2$, —O—$(C_2H_4O)_q R^1$, —(C═O)—O—$C_{1-4}$alkyl and —O—(C═O)$C_{1-4}$alkyl; wherein $R^1$ is H or $C_{1-4}$ alkyl; $R^2$ is —COOH, —$SO_3H$, or —$OPO_3H_2$; wherein q is an integer from 1 to 4; and wherein the group W may be in the form of a pharmaceutically acceptable salt; and (b) a pyridyl group; which is optionally in the form of a pyridinium ion; and wherein either the first pendant group is coupled to the PVA through an ether linkage and the second pendant group is coupled to the PVA through a 1,3 dioxane group or both the first pendant group and the second pendant group are coupled to the PVA through a 1,3 dioxane group.

12. A medical device according to claim 11, wherein the first pendant group is of the formula 4A and the second pendant group is of the formula 4B:

4A

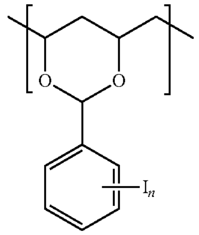

4B

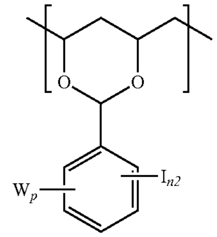

wherein n is an integer from 1 to 4; n2 is an integer from 1 to 4; W is selected from —$SO_3H$, —O—($C_{1-4}$alkyl) $SO_3H$ and —COOH; p is 1 or 2.

13. A medical device according to claim 11, wherein the first pendant group is of the formula 4A and the second pendant group is of the formula 4D:

4A

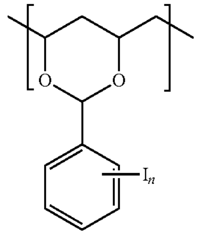

4D

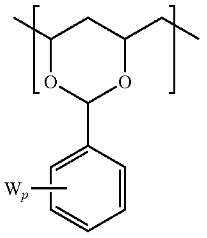

wherein n is an integer from 1 to 4; W is selected from —$SO_3H$ and —COOH; and p is 1 or 2.

14. A medical device according to claim 11, wherein the first pendant group is of the formula 4A and the second pendant group is of the formula 4E

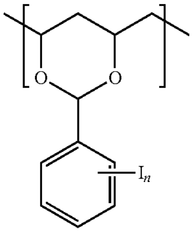

4A

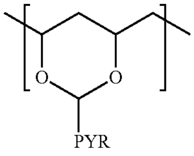

4E wherein n is an integer from 1 to 4; W is selected from —$SO_3H$ and —COOH; p is 1 or 2; and PYR is a pyridyl group.

15. A medical device according to claim 4 wherein n is 2 or 3.

16. A medical device according to claim 5 wherein p is one.

17. A medical device according to claim 1 wherein the PVA without the first and second pendant groups has a weight average molecular weight of 1 kDa to 250 kDa.

18. A medical device according to claim 1 wherein the PVA without the first and second pendant groups has a weight average molecular weight of 10 kDa to 100 kDa.

19. A medical device according to claim 1 having an iodine content of at least 10% dry weight.

20. A medical device according to claim 1, having a radiodensity of at least 500 HU.

* * * * *